(12) United States Patent
Cavalla

(10) Patent No.: US 9,610,291 B2
(45) Date of Patent: Apr. 4, 2017

(54) TREATMENT OF RESPIRATORY DEPRESSION

(71) Applicant: NUMEDICUS LIMITED, Cambridgeshire (GB)

(72) Inventor: David Cavalla, Cambridgeshire (GB)

(73) Assignee: Numedicus Limited, Cambridge (GB)

( * ) Notice: Subject to any disclaimer, the term of this patent is extended or adjusted under 35 U.S.C. 154(b) by 0 days.

(21) Appl. No.: 14/400,343

(22) PCT Filed: May 10, 2013

(86) PCT No.: PCT/GB2013/051213
§ 371 (c)(1),
(2) Date: Nov. 11, 2014

(87) PCT Pub. No.: WO2013/167906
PCT Pub. Date: Nov. 14, 2013

(65) Prior Publication Data
US 2015/0141405 A1    May 21, 2015

(30) Foreign Application Priority Data

May 11, 2012 (GB) .................. 1208315.0

(51) Int. Cl.
*A61K 31/554* (2006.01)
*C07D 281/02* (2006.01)
*A61K 45/06* (2006.01)
*A61K 31/485* (2006.01)

(52) U.S. Cl.
CPC .......... *A61K 31/554* (2013.01); *A61K 31/485* (2013.01); *A61K 45/06* (2013.01)

(58) Field of Classification Search
CPC ........................ A61K 31/554; C07D 281/02
USPC ...................... 514/211.13; 540/549
See application file for complete search history.

(56) References Cited

PUBLICATIONS

Greer J J et al.; "Ampakine therapy to counter fentanyl-induced respiratory depression", Respiratory Physiology and Neurobiology, vol. 168. No. 1-2. Aug. 31, 2009, pp. 153-157.
M. Ogier et al.; "Brain-Derived Neurotrophic Factor Expression and Respiratory Function Improve after Ampakine Treatment in a Mouse Model of Rett Syndrome". Journal of Neuroscience, vol. 27. No. 40, Oct. 3, 2007, pp. 10912-10917.
Viktor Szegedi et al.; "Tianeptine potentiates AMPA receptors by activating CaMKII and PKA via the p38. p42144 MAPK and JNK pathways". Neurochemistry International. Pergamon Press, vol. 59. No. 8, Oct. 17, 2011, pp. 1109-1122.
Lechin F et al.; "Treatment of bronchial asthma with tianeptine"; Methods and Findings in Experimental and Clinical Pharmacology, Prous Science, vol. 26. No. 9, Jan. 1, 2004, pp. 697-701.
Database Medline [Online]; US National Library of Medicine (NLM). Bethesda. MD. US; Sep. 2010, Chu Chin-Chen et al: "Tianeptine reduces morphine antinociceptive tolerance and physical dependence", XP002711616. Database accession No. NLM20679893 abstract & Behavioural Pharmacology Sep 2010. vol. 21. No. 5-6, Sep. 2010, pp. 523-529.
PCT/GB2013/051213; PCT International Search Report dated Aug. 22, 2013.

*Primary Examiner* — Brenda Coleman
(74) *Attorney, Agent, or Firm* — McCarter & English, LLP

(57) ABSTRACT

Tricyclic dibenzothiazepine compounds for use in the treatment of respiratory depression.

18 Claims, 3 Drawing Sheets

TREATMENT OF RESPIRATORY DEPRESSION

The present application is a U.S. National Stage Application based on and claiming benefit and priority under 35 U.S.C. §371 of International Application No. PCT/GB2013/051213 filed 10 May 2013, which in turn claims benefit of and priority to Great Britain Application No. 1208315.0 filed 11 May 2012, the entirety of each of which is hereby incorporated herein by reference.

The present invention relates to tricyclic dibenzothiazepine type compounds for use in the treatment of respiratory depression in a subject (i.e. a mammal such as an animal or human, especially a human) as a result of a medical condition or pharmacological agents such as opiates, opioids or barbiturates. In particular, although not exclusively, the present invention relates to a alleviating respiratory depression with 7-[(3-chloro-6,11-dihydro-6-methyl-dibenzo[c,f][1,2]thiazepin-11-yl)amino]heptanoic acid S,S-dioxide (tianeptine) and/or its MC5 metabolite (7-[(3-chloro-6,1'-dihydro-6-methyl-dibenzo[c,f][1,2]thiazepin-11-yl)amino]pentanoic acid S,S-dioxide) in a subject as a result of a medical condition or pharmacological agents such as opiates, opioids or barbiturates. Additionally, the present invention relates to pharmaceutical compositions including tricyclic dibenzothiazepine type compounds and the use of such compositions as a medicament, particularly a human medicament.

Tianeptine, as depicted below, is originally described in French patent 2,104,728 and has been reported that it may be used in the treatment of neurodegenerative pathologies, neuropathic pain, fibromyalgia, chronic fatigue syndrome and irritable bowel syndrome.

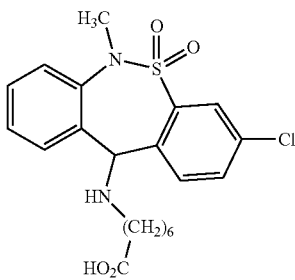

Opiates are known to reduce respiratory rate and inspirational volume, as well as reduce sensitivity to $CO_2$; $\mu$- and $\delta$-opioid receptors as well as their endogenous ligands are present in essentially all respiratory regions of the pons and medulla. Exogenous application of opioids has also been shown both in vivo and in vitro to depress inspiratory and expiratory neuronal activity.

Because opiates depress breathing, their use is contraindicated in many instances, especially in patients with compromised cardiovascular and pulmonary function. Respiratory depression, otherwise known as respiratory insufficiency or hypoventilation, is often a limiting factor in the degree of analgesia that a patient may receive. Thus, there is an outstanding need to produce the analgesia of the opiates and opioids, without depressing the respiratory function of the patient.

In addition to the disturbance of respiratory rhythm as a result of drugs, abnormalities as a consequence of a medical condition, such as hypoventilation in association with obesity or irregular breathing during sleep, are also increasingly recognized clinically as potentially having serious health consequences. One of the most common physiological conditions involving disturbance of respiratory rhythm is sleep apnea, which may be of an obstructive, central or mixed pathophysiology.

Obstructive sleep apnea (OSA) primarily involves the loss of tone in the genioglossus muscle of the tongue, which is innervated by the hypoglossal nerve, causing sufferers to stop breathing (apnea), often hundreds of times per night and sometimes for a minute or longer. As many as 20% of adults have at least mild OSA, and at least 2% of women and 4% of men have moderate to severe OSA. OSA is associated with a variety of health risks, such as central hypoxia, which leads to activation of the sympathetic nervous system, resulting in acute hypertension and tachycardia; it can also lead to sleep arousal and poor sleep quality, resulting in daytime fatigue, potentially with serious consequences, such as falling asleep while driving. Chronically, repeated hypoxia and spiking blood pressure cause increased propensity for neurocognitive impairment, hypertension, myocardial infarction and stroke. Chronic snoring is another sleep disorder which often predicts the development of OSA. In central sleep apnea, the brain's respiratory control centers are imbalanced during sleep, and commonly patients with this condition repeatedly stop breathing during sleep. A form of central sleep apnea commonly occurs in people with congestive heart failure. Obesity hypoventilation syndrome (OHS), also known as Pickwickian syndrome, is an under-recognised condition related to, but also potentially occurring separately from, OSA. Its origin has been hypothesised to involve problems in mobilizing the chest wall and diaphragm, leading to ineffective gas exchange, and consequent low levels of blood oxygen saturation, with concomitant high levels of blood $CO_2$.

Patients with sleep apnea or snoring may be provided with machines providing continuous positive airway pressure (CPAP), intrusive dental appliances, or reconstructive surgery to reshape the patient's upper airway to reduce obstructions. However, CPAP and appliances typically have a low level of patient compliance, and surgery is often ineffective in the long term. Treatment for OHS also involves mechanical ventilation (e.g. BiPAP), but this is also not entirely satisfactory and is associated with low levels of patient compliance.

It is also important to recognise that patients using opioids are at risk for disorders of breathing during sleep including central and obstructive apneas, hypopneas, ataxic breathing and non-apneic hypoxemia.

Accordingly, there is a need to reduce, inhibit or prevent respiratory depression in a subject which may result as a result of drug administration or due to abnormalities as a consequence of a medical condition.

DETAILED DESCRIPTION OF THE INVENTION

Figure 1:
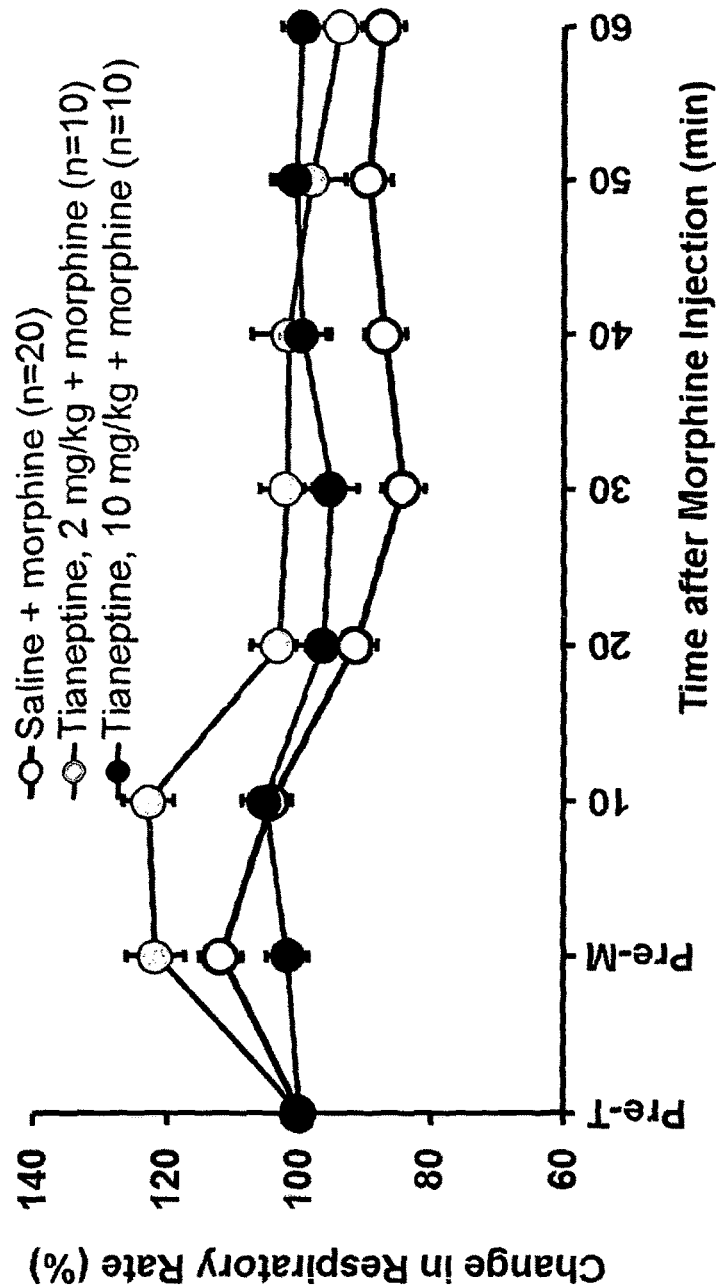
FIG. 1 depicts the change in respiratory rate for (a) animals injected with morphine (10 mg/kg intramuscular) and saline only; (b) animals injected with tianeptine (2 mg/kg ip) and followed by morphine (10 mg/kg intramuscular); and (c) animals injected with tianeptine (2 mg/kg ip) and followed by morphine (10 mg/kg intramuscular).

According to a first aspect, the present invention provides a compound of formula (I), or a pharmaceutically or veterinarily acceptable salt thereof, or a pharmaceutically or veterinarily acceptable solvate of either entity or a pharmaceutical or veterinary composition containing any of the foregoing for use in the treatment of respiratory depression in a subject (i.e. mammal such as an animal or human, especially a human), wherein a compound of formula (I) comprises:

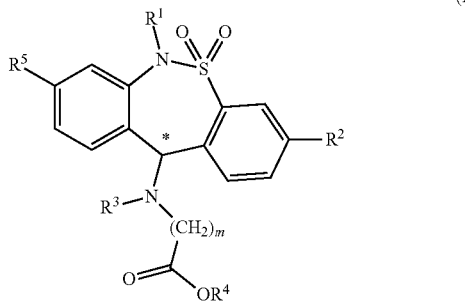

(I)

wherein:
$R^1$ and $R^3$ each independently represent, at each occurrence when used herein, H or $C_1$ to $C_6$ alkyl;
$R^2$ and $R^5$ each independently represent, at each occurrence when used herein, H or halo;
$R^4$ represents H or $C_1$ to $C_6$ alkyl; and,
m is an integer of 2 to 12 inclusive.

By the term "treatment" or "treating" as used herein, we include both therapeutic (curative), palliative and prophylactic treatment. Suitably, the treatment of respiratory depression is accomplished by administration of a therapeutically effective amount of a compound of formula (I), or a pharmacologically active metabolite thereof, or a pharmaceutically or veterinarily acceptable salt thereof, or a pharmaceutically or veterinarily acceptable solvate of either entity or a pharmaceutical or veterinary composition containing any of the foregoing to the subject. The term "effective amount" or "therapeutically effective amount" as used herein refers to the amount or dosage of an agent sufficient to effectuate a desired therapeutic effect. Such amount may vary depending on the effect to be achieved, the agent used and the body weight of the subject. Typically, a therapeutically effective amount of a compound of formula (I), or a pharmacologically active metabolite thereof, or a pharmaceutically or veterinarily acceptable salt thereof, or a pharmaceutically or veterinarily acceptable solvate of either entity to be administered is 2 to about 600 mg/day, preferably from about 5 to about 400 mg/day, and more preferably about 10 to 300 mg/day.

Preferably, $R^1$ in a compound of formula (I) represents $C_1$ to $C_6$ alkyl, more preferably, $R^1$ represents $C_1$ to $C_4$ alkyl, even more preferably linear $C_1$ to $C_4$ alkyl. Most preferably, $R^1$ represents a methyl group.

Preferably, $R^2$ in a compound of formula (I) is H, fluoro or chloro, more preferably H or chloro. Most preferably, $R^2$ is chloro.

Preferably, $R^3$ in a compound of formula (I) represents H or $C_1$ to $C_4$ alkyl. More preferably, $R^3$ represents H or linear $C_1$ to $C_4$ alkyl. Most preferably, $R^3$ represents H.

Preferably, $R^4$ in a compound of formula (I) represents H or $C_1$ to $C_4$ alkyl. Most preferably, $R^4$ in a compound of formula (I) represents H.

Preferably, $R^5$ in a compound of formula (I) is H, fluoro or chloro, more preferably H or chloro. Most preferably, $R^5$ represents H.

Preferably, m in a compound of formula (I) is an integer from 2 to 8 inclusive, more preferably 2 to 6 inclusive, especially 4 to 6. Most preferably, m is 4 or 6, especially 6.

Thus, the most preferred compounds of formula (I) are: tianeptine (7-[(3-chloro-6,1'-dihydro-6-methyl-dibenzo[c,f][1,2]thiazepin-11-yl)amino]heptanoic acid S,S-dioxide) wherein $R^1$ is methyl, $R^2$ is chloro, $R^3$ is hydrogen, $R^4$ is hydrogen, $R^5$ is hydrogen, and m is 6 in a compound of formula (I); or the pharmacological active metabolite of tianeptine, referred to as the "MC5 metabolite" (7-[(3-chloro-6,1'-dihydro-6-methyl-dibenzo[c,f][1,2]thiazepin-11-yl)amino]pentanoic acid S,S-dioxide) wherein $R^1$ is methyl, $R^2$ is chloro, $R^3$ is hydrogen, $R^4$ is hydrogen, $R^5$ is hydrogen, and m is 4 in a compound of formula (I).

Tianeptine, which has the systematic name 7-[(3-chloro-6,1'-dihydro-6-methyl-dibenzo[c,f][1,2]thiazepin-11-yl)amino]heptanoic acid S,S-dioxide, is a tricyclic anti-depressant of the dibenzothiazepine type. A sodium salt of tianeptine is currently marketed in Europe under the trademark Stablon®. Tianeptine is known to have psychostimulant, antidepressive, analgesic, antitussive, antihistaminic and gastric antisecretory properties. The suggested daily dosage of tianeptine is 37.5 mg, to be given in divided doses three times daily, due to its short duration of action. Tianeptine has a plasma half-life of 2.5+/−1.1 h in humans.

As defined herein, the term "$C_1$ to $C_6$ alkyl", which $R^1$, $R^3$ and $R^4$ may each independently represent, may unless otherwise specified, when there is a sufficient number of carbon atoms, be linear or branched, be cyclic, acylic or part cyclic/acyclic. Preferably, the alkyl group is an acyclic alkyl group, more preferably a linear alkyl group. Representative examples of alkyl groups include, but are not limited to, methyl, ethyl, n-propyl, iso-propyl, n-butyl, sec-butyl, iso-butyl, tert-butyl, n-pentyl, iso-pentyl, neo-pentyl and hexyl.

The term "halo", when used herein, includes fluoro, chloro, bromo and iodo.

For the avoidance of doubt each $R^1$, $R^2$, $R^3$, $R^4$ and $R^5$ group referred to herein is independent of other $R^1$, $R^2$, $R^3$, $R^4$ and $R^5$ groups, respectively. For example, if $R^1$ and $R^3$ both represent $C_1$ to $C_6$ alkyl then the two individual alkyl substituents are independent of one another, and not necessarily identical (though this possibility is not excluded).

The compounds of formula (I), contain one or more asymmetric carbon atoms and therefore exist in two or more stereoisomeric forms. In a compound of formula (I) the aliphatic carbon marked with an asterisk (*) denotes an asymmetric carbon atom and the absolute configuration about that carbon may be (R)- or (S)- as designated according to the Cahn Ingold Prelog system. The present invention includes the individual (R)- and (S)-enantiomeric forms of the compounds of formula (I), in respect of the aliphatic carbon marked with an asterisk (*), and mixtures thereof (e.g. racemates). In accordance with a preferred embodiment, the present invention includes the individual (R)- and (S)-enantiomeric forms of the compounds of formula (I), in respect of the aliphatic carbon marked with an asterisk (*). Accordingly, such individual (R)- and (S)-enantiomeric forms possess optical activity.

As used herein, the individual enantiomeric forms of racemates refer to compositions consisting substantially of a single stereoisomer, i.e. substantially free of the other stereoisomer, that is containing at least 80%, preferably at least 90%, more preferably at least 95%, and even more preferably at least 98% by weight of such a single stereoisomer. Thus, the term "(R)-enantiomeric form substantially free of the (S)-enantiomeric form" means a compound that comprises at least 80% or more by weight of the (R)-enantiomer (preferably at least 90%, more preferably at least 95%, and even more preferably at least 98% by weight of the (R)-enantiomer), and likewise contains 20% or less by weight of the (S)-enantiomer (preferably less than 10%, more preferably less than 5%, and even more preferably less than 2% by weight of the (S)-enantiomer) as a contaminant. By "(S)-enantiomeric form substantially free of the (R)-enantiomeric form" is meant a compound that comprises at least 80% or more by weight of the (S)-enantiomer (preferably at least 90%, more preferably at least 95%, and even more preferably at least 98% by weight of the (S)-enantiomer), and likewise contains 20% or less by weight of the (R)-enantiomer (preferably less than 10%, more preferably less than 5%, and even more preferably less than 2% by weight of the (R)-enantiomer) as a contaminant.

As used herein, "optically active" refers to a property whereby a material rotates the plane of plane-polarized light. A compound that is optically active is non-superimposable on its mirror image. As used herein, the property of non-superimposability of an object on its mirror image is called "chirality." The most common structural feature producing chirality is an asymmetric carbon atom; i.e., a carbon atom having four nonequivalent groups attached thereto.

As used herein, "enantiomer" refers to each of the two non-superimposable isomers of a pure compound that is optically active. Single enantiomers are designated according to the Calm-Ingold-Prelog system, which is a well-known set of priority rules for ranking the four groups attached to an asymmetric carbon. See, e.g., March, Adv Org Chem 4th Ed., (1992), p. 109.

As used herein, "racemate" or "racemic compound" refers to a 50-50 mixture of two enantiomers such that the mixture does not rotate plane-polarized light.

An individual enantiomer of a compound of formula (I), particularly a compound of formula (I) in respect of the aliphatic carbon marked with an asterisk (*), may be prepared from the corresponding optically pure intermediate or by resolution, either by HPLC of the racemate using a suitable chiral support or, where appropriate, by fractional crystallisation of the diastereoisomeric salts formed by reaction of the racemate with a suitable optically active acid or base.

It will be appreciated that the compounds of the invention may include one or more further asymmetric carbon atoms, in addition to the aliphatic carbon marked with an asterisk (*) in a compound of formula (I), depending on the identity of each of the substituent groups $R^1$, $R^2$, $R^3$, $R^4$ and $R^5$. For the avoidance of doubt, all stereoisomers and diastereoisomers of the compounds of formula (I) are included within the scope of the invention.

Thus according to a preferred embodiment, the compound of formula (I) represents tianeptine as defined hereinbefore, particularly (R)-tianeptine, substantially free of the corresponding (S)-enantiomeric form, with respect to the carbon marked with an asterisk (*) in a compound of formula (I) or (S)-tianeptine, substantially free of the corresponding (R)-enantiomeric form, with respect to the carbon marked with an asterisk (*) in a compound of formula (I).

Thus according to a further preferred embodiment, the compound of formula (I) represents the MC5 metabolite of tianeptine as defined hereinbefore, particularly the (R)-enantiomeric form, substantially free of the corresponding (S)-enantiomeric form, with respect to the carbon marked with an asterisk (*) in a compound of formula (I) or the (S)-enantiomeric form, substantially free of the corresponding (R)-enantiomeric form, with respect to the carbon marked with an asterisk (*) in a compound of formula (I).

To isolate the individual (R)- and (S)-enantiomers of tianeptine from the racemate, the racemate must be resolved. This resolution can be achieved by converting racemic tianeptine into a pair of diastereomers, for example by covalently bonding to an optically active moiety or by salt formation with an optically active base or acid. Either method provides a molecule with a second chiral center, thus generating a pair of diastereomers. The diastereomeric pair can then be separated by conventional methods, such as crystallization or chromatography.

Racemic tianeptine can also be separated into enantiomers without diastereomer formation, for example, by differential absorption on a chiral stationary phase of a chromatography (e.g., HPLC) column. Preparative HPLC columns suitable for diastereomer separation are commercially available with a variety of packing materials to suit a broad range of separation applications. Stationary phases suitable for resolving tianeptine include: (i) macrocyclic glycopeptides, such as silica-bonded vancomycin which contains 18 chiral centers surrounding three pockets or cavities; (ii) chiral $\alpha_1$-acid glycoprotein; (iii) human serum albumin; and (iv) cellobiohydrolase (CBH).

The compounds of formula (I) as defined herein, such as tianeptine and the MC5 metabolite, may be prepared by known synthetic procedures, for example as described in: French patent 2,104,728; GB patent application 1,269,551; U.S. Pat. Nos. 4,766,114, 3,758,528 and 3,821,249, all of Malen et al.; and U.S. Pat. No. 6,441,165 of Blanchard et al.

The pharmaceutically or veterinarily acceptable salts of the compounds of formula (I) are, for example, non-toxic acid addition salts formed with inorganic acids or organic acids or base addition salts. Suitable inorganic acids include hydrochloric, hydrobromic, hydroiodic, nitric, carbonic, sulfuric and phosphoric acid. Suitable organic acids include aliphatic, cycloaliphatic, aromatic, araliphatic, heterocyclic, carboxylic and sulfonic classes of organic acids, such as formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, salicylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, beta-hydroxybutyric, galactaric and galacturonic acid.

Suitable pharmaceutically acceptable base addition salts of the compounds of formula (I) include metallic salts made from calcium, magnesium, potassium, sodium and zinc, or organic salts made from N,N'-dibenzylethylenediamine, chloroprocaine, choline, diethanolamine, ethylenediamine, meglumine (N-methylglucamine), arginine and procaine. Compounds of formula (I), e.g. tianeptine, may also form a base addition salt with a basic opiate compound such as morphine, oxycodone, dihydrocodeine, hydrocodone or fentanyl.

The pharmaceutically acceptable acid addition salts of the compounds of formula (I) may be prepared in a conventional manner. For example, a solution of the free base is treated with the appropriate acid, either neat or in a suitable solvent, and the resulting salt isolated either by filtration or by evaporation under vacuum of the reaction solvent. Pharmaceutically acceptable base addition salts can be obtained in an analogous manner by treating a solution of a compound of formula (I) with the appropriate base. Both types of salt may be formed or interconverted using ion-exchange resin techniques. For a review on suitable pharmaceutical salts see Berge et. al., J. Pharm., Sci., 66, 1-19, 1977. A highly preferred salt is the sodium salt.

The pharmaceutically or veterinarily acceptable solvates of the compounds of formula I include the hydrates thereof.

Also included in the invention are radiolabelled and isotopically labeled derivatives of the compounds of formula (I) which are suitable for biological studies. Examples of such derivatives include, but are not limited to, $^{2}H$, $^{3}H$, $^{11}C$, $^{13}C$, $^{14}C$, $^{15}N$, $^{17}O$, $^{18}O$, $^{18}F$, $^{35}S$ and $^{36}Cl$.

Certain compounds of formula (I) may exist in multiple crystalline or amorphous forms. All physical forms and polymorphs are included within the scope of the invention.

It will be appreciated by those skilled in the art that certain derivatives of compounds of formula (I) may not possess pharmacological activity as such, but may, in certain instances, be administered orally or parenterally and thereafter metabolized in the body to form compounds of formula (I) which are pharmacologically active. Such derivatives may therefore be described as "prodrugs". Further, certain compounds of formula (I) may act as prodrugs of other compounds of formula (I). All prodrugs, of compounds of formula (I) are included within the scope of the invention.

Additionally, the compound of formula (I) may be metabolized in the body of the subject to form an active metabolite. The administration of such metabolites to treat respiratory depression is also contemplated within the scope of the invention. Tianeptine is metabolised to 7-[(3-chloro-6,1'-dihydro-6-methyl-dibenzo[c,f][1,2]thiazepin-11-yl)amino]pentanoic acid S,S-dioxide, an active metabolite known as the "MC5 metabolite". Thus, according to a preferred aspect the present the present invention extends to the use of tianeptine and the MC5 metabolite, or a pharmaceutically or veterinarily acceptable solvate of either entity or a pharmaceutical or veterinary composition containing any of the foregoing for the treatment of respiratory depression in mammal, such as an animal or human, especially a human.

Medical Use

The compounds of formula (I) are useful because they possess pharmacological activity for the treatment of respiratory depression or hypoventilation in a subject (i.e. mammals, especially humans). They are therefore indicated as pharmaceuticals, as well as for use as animal medicaments for reducing or inhibiting respiratory depression in animals and humans.

The phrase "respiratory depression" or "hypoventilation" as used herein refers to a variety of conditions characterized by reduced respiratory frequency and inspiratory drive to cranial and spinal motor neurons. Specifically, respiratory depression refers to conditions where the medullary neural network associated with respiratory rhythm generating activity does not respond to accumulating levels of $pCO_2$ (i.e. $CO_2$ partial pressure), or decreasing levels of $pO_2$, in the blood and subsequently understimulates motorneurons controlling lung musculature.

The terms "reducing" or "inhibiting" as used herein refers to a reduction in respiratory depression in a subject in the presence of a compound of formula (I), preferably tianeptine, as compared with the level of respiratory depression in the absence of such a compound.

By the term "subject" as referred to herein we mean "a mammal" which includes animals and humans, especially humans. The term "mammal" therefore may also include domestic and common laboratory mammals such as non-human primates, horses, pigs, goats, sheep, dogs, cats, rabbits, mice, rats, and the like. The most preferred mammal is a human subject.

The methods and compositions of the present invention are directed toward subjects having respiratory depression. The causes of respiratory depression that can be treated with the methods and compositions disclosed herein are varied, and include drug overdose, pharmaceutical use of central respiratory depressants, and medical conditions, including trauma.

Where the respiratory depression results from a drug overdose, such drugs taken in excess include opiates, opioids, barbiturates, benzodiazepines, alcohol, non-benzodiazepine GABA-A modulators (such as zaleplon zopiclone, and zolpidem), deliriants (such as atropine, diphenhydramine hydrochloride, dimenhydrinate, and scopolamine), dissociative anaesthetics (such as: fluorathane and related volatile anaesthetics, dextromethorphan, ketamine, nitrous oxide, phencyclidine and salvinorin A).

Such drugs may be referred to "central respiratory depressants". The term "central respiratory depressant" as used herein refers to any compound that acts on the central nervous system resulting in respiratory depression or hypoventilation. Typical central respiratory depressants can include drugs such as alcohol, benzodiazepines, barbiturates, GHB (gamma hydroxy-butyric acid), opioids and opiates all of which can produce respiratory depression when taken in sufficient dosage.

The term "central nervous system" or "CNS" as used herein comprises the brain and the spinal cord. The term "peripheral nervous system" or "PNS" comprises all parts of the nervous system that are not part of the CNS, including the cranial and spinal nerves, and the autonomic nervous system.

The term "opiate" and "opioid" as used herein refer generically to a class of narcotic compounds characterized by having addiction-forming or addiction-sustaining properties similar to morphine or being capable of conversion into a drug having such addiction-forming or addiction-sustaining properties. Specifically, the term "opiate" denotes compounds containing the fundamental morphine or thebaine structure and possessing some affinity to any, or all, of the opioid receptor subtypes. Examples of opiates are heroin, and buprenorphine. An "opioid" is any compound, peptide or otherwise, which, while not containing the fundamental morphine or thebaine structure, possesses some affinity for any, or all, of the opioid receptor subtypes. Common opioids are endorphin, fentanyl and methadone. A non-exclusive list of opiates and opioids includes: alfentanil, buprenorphine, carfentanil, codeine, dihydrocodeine, diprenorphine, ecgonine, etorphine, fentanyl, heroin, hydrocodone, hydromorphone, laevo-alpha-acetylmethadol (LAAM), levorphanol, meperidine, methadone, morphine, nalbuphine, beta-hydroxy-3-methylfentanyl, oxycodone, oxymorphone, pentazocine, propoxyphene, remifentanil, sufentanil, thebaine, tilidine, and tramadol. The definition includes all opiates and opioids, from any source, including naturally-derived compounds, synthetic compounds, and semi-synthetic compounds. The definition also includes all isomers, stereoisomers, esters, ethers, salts, and salts of such isomers, stereoisomers, esters, and ethers, whenever the existence of such isomers, stereoisomers, esters, and ethers is possible within the specific chemical designation.

The term "barbiturate" as used herein refers generically to a salt or ester of barbituric acid and includes any of a group of barbituric acid derivatives that act as central nervous system depressants and are used as sedatives or hypnotics. Non-limiting exemplary barbiturates include: allobarbital, amylbarbital, butabarbital, hexabarbital, mephobarbital, methohexital, pentobarbital, phenobarbital, phenethylbarbital, secobarbital, talbutal, and thiopental. The definition also includes all isomers, stereoisomers, esters, ethers, salts, and salts of such isomers, stereoisomers, esters, and ethers, whenever the existence of such isomers, stereoisomers, esters, and ethers is possible within the specific chemical designation.

The term "benzodiazepine" as used herein refers generically to a class of drugs that act as central nervous system depressants with sedative, hypnotic, anxiolytic, anticonvulsant, muscle relaxant, and amnesic actions through the positive modulation of the GABA-A receptor complex. Non-limiting exemplary benzodiazepines include alprazolam, clonazepam, diazepam, flunitrazepam, lorazepam, nitrazepam, and temazepam.

Thus according to a preferred embodiment, the respiratory depression in the subject (i.e. mammal) results from administration of a central respiratory depressant to the subject. Preferably, the central respiratory depressant is an opioid or opiate, especially an opiate, such as morphine.

Where the respiratory depression occurs in a subject (i.e. mammal, such as a human) having a medical condition, such exemplary medical conditions include for example central sleep apnea, stroke-induced central sleep apnea, obstructive sleep apnea, sleep apnea resulting from Parkinson's disease, congenital hypoventilation syndrome, obesity hypoventilation syndrome, sudden infant death syndrome, Rett's syndrome, Cheyne-Stokes respiration, Biot's breathing, Ondine's curse, and Prader-Willi's syndrome. In some embodiments, the subject has respiratory depression as a result of a traumatic injury or neurodegenerative disease, for instance spinal cord injury or traumatic brain injury. Non-limiting exemplary neurodegenerative diseases include Parkinson's disease, progressive supranuclear palsy, spinal muscular atrophy, amyotrophic lateral sclerosis, Huntington's disease and stroke.

Thus according to an alternative embodiment, the respiratory depression results from the subject having a medical condition, such as those medical conditions as defined herein, especially Rett's syndrome.

Certain subjects are at particular risk for drug-induced respiratory depression, including the morbidly obese, patients with sleep apnea, patients with specific neuromuscular diseases, the very young (premature babies, children with breathing problems during sleep), the very old, and the very ill. In addition, patients with an extensive Cyp2D6 genotype can rapidly metabolise certain opiates, giving rise to an abnormally high level of an active metabolite, and can suffer enhanced respiratory depression as a result. Certain patient groups are at high risk for sleep apnea, including the overweight and obese, patients with small nasal passages and mouths or throats, or enlarged tonsils. Sleep apnea is also more common in patients with nasal congestion, as well as in older patients or smokers.

Exemplary causes of respiratory depression that can be treated using the methods and compositions as disclosed herein are described above. Respiratory depression in a subject can in some circumstances be recognised by a person skilled in the art by direct observation. One of the symptoms of respiratory depression is hypopnea, which is characterized by a slow or shallow respiratory rate; this becomes clinically significant hypopnea when it reaches a 50% or greater reduction in air flow and a 3% or greater desaturation in blood $O_2$ levels for 10 seconds or longer. A subject having respiratory depression may also show signs of cyanosis, which is a bluish coloration of the skin due to the presence of deoxygenated hemoglobin in blood vessels near the skin surface, arising when the oxygen saturation of arterial blood falls below 85%.

A polysomnogram may also be used to diagnose respiratory depression, typically with subjects suspected of having some form of sleep apnea or sleep-disturbed respiratory rhythm. Respiratory acidosis (a PaCO2>6.3 kPa or 47 mm Hg and a pH of 7.35) is another symptom of respiratory depression. Respiratory depression can also be monitored using pulse oximetry. Respiratory airflow can be monitored with a nasal cannula connected to a pressure transducer, and thoracic and abdominal respiratory movements are routinely monitored with piezoelectric strain gauges, particularly in newborn infants.

A person of ordinary skill in the art will be able to recognize respiratory depression in a subject using the methods as described above, and thereby administer a compound of formula (I), e.g. tianeptine, in a therapeutically effective amount to reduce or inhibit the respiratory depression to a subject in need of treatment.

Thus the invention provides a method of treating, such as reducing or inhibiting, respiratory depression in a subject (i.e. mammal) in need of such treatment comprising administering to the subject a therapeutic effective amount of a compound of formula (I) as defined herein, or a pharmaceutically or veterinarily acceptable salt thereof, or a pharmaceutically or veterinarily acceptable solvate of either entity or a pharmaceutical or veterinary composition containing any of the foregoing. Preferably, the compound of formula (I) is tianeptine or the MC5 metabolite.

Thus the invention also provides the use of a compound of formula (I), or a pharmaceutically or veterinarily acceptable salt thereof, or a pharmaceutically or veterinarily acceptable solvate of either entity or a pharmaceutical or veterinary composition containing any of the foregoing for the treatment of respiratory depression in a subject (i.e. mammal). Preferably, the compound of formula (I) is tianeptine or the MC5 metabolite.

Pharmaceutical and Veterinary Preparations

The compounds of formula (I) will normally be administered orally or by any parenteral route in the form of pharmaceutical preparations comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

One skilled in the art can readily determine an effective amount of a compound of formula (I) to be administered, by taking into account factors such as the size, weight, age and sex of the subject, the extent of disease penetration or persistence and severity of symptoms, and the route of administration. Generally, an effective amount of a compound of formula (I), such as tianeptine, administered to a subject is from about 2 to about 600 mg/day, preferably from about 5 to about 400 mg/day, and more preferably about 10 to 300 mg/day. Higher or lower doses are also contemplated.

The compound of formula (I) can be administered to a subject by any route, for example by enteral (e.g., oral, rectal, intranasal, etc.) and parenteral administration. Parenteral administration includes, for example, intravenous, intramuscular, intraarterial, intraperitoneal (ip), intravaginal, intravesical (e.g., into the bladder), intradermal, topical or subcutaneous administration. Also contemplated within the scope of the invention is the instillation of the compound of formula (I) into the body of the subject, for example in a controlled release formulation, with systemic or local release of the compound to occur over time or at a later time. Preferably, the compound of formula (I), e.g. tianeptine, is localized in a depot for controlled release to the circulation or to a local site such as the gastrointestinal tract.

A compound of formula (I), e.g. tianeptine, can be administered together with a pharmaceutically or veterinarily acceptable carrier. Pharmaceutical and veterinary formulations can comprise from 0.1 to 99.99, preferably 2 to 50, more preferably 5 to 30, weight percent of a compound of formula (I), e.g. tianeptine. The pharmaceutical compositions can be formulated according to standard practices in the field of pharmaceutical preparations. See Alphonso Gennaro, ed., Remington's Pharmaceutical Sciences. 18th Ed., (1990) Mack Publishing Co., Easton, Pa. Suitable dosage forms can comprise, for example, tablets, capsules, solutions, parenteral solutions, troches, suppositories, or suspensions.

By "pharmaceutically or veterinary acceptable carrier, adjuvant or diluent" is meant any diluent or excipient that is compatible with the other ingredients of the composition, and which is not deleterious to the recipient. The pharmaceutically acceptable carrier can be selected on the basis of the desired route of administration, in accordance with standard pharmaceutical practices.

Pharmaceutical and veterinary compositions for parenteral administration can take the form of an aqueous or nonaqueous solution, dispersion, suspension or emulsion. In preparing pharmaceutical and veterinary compositions for parenteral administration, a compound of formula (I), e.g. tianeptine, can be mixed with a suitable pharmaceutically or veterinarily acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical and veterinary compositions for parenteral administration preferably contain a water-soluble salt of the compound of formula (I), e.g. tianeptine. Stabilizing agents, antioxidizing agents and preservatives can also be added to the pharmaceutical and veterinary compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions for oral administration, the compound of formula (I), e.g. tianeptine, can be combined with one or more solid or liquid inactive ingredients to form tablets, capsules, pills, powders, granules or other suitable oral dosage forms. For example, the compound of formula (I), e.g. tianeptine, can be combined with at least one pharmaceutically acceptable carrier such as a solvent, filler, binder, humectant, disintegrating agent, solution retarder, absorption accelerator, wetting agent absorbent or lubricating agent. In one embodiment, the compound of formula (I), e.g. tianeptine, is combined with carboxymethylcellulose calcium, magnesium stearate, mannitol and starch, and is formed into tablets by conventional tableting methods.

In one embodiment, controlled-release pharmaceutical compositions comprise the compound of formula (I), e.g. tianeptine, and a controlled-release component. Preferably, a controlled-release pharmaceutical composition is capable of releasing the compound of formula (I), e.g. tianeptine, into a subject at a desired rate, so as to maintain a substantially constant pharmacological activity for a given period of time. As used herein, a "controlled-release component" is a compound such as a polymer, polymer matrix, gel, permeable membrane, liposome and/or microsphere that induces the controlled-release of the compound of formula (I), e.g. tianeptine, into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, tianeptine is incorporated into a sol-gel matrix that is a solid at room temperature. This sol-gel matrix is implanted into a subject having a body temperature high enough to induce gel formation of the sol-gel matrix, thereby releasing the active ingredient into the subject. Suitable controlled release formulations are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer) and U.S. Pat. No. 5,888,542 (matrix tablet allowing the prolonged release of the sodium salt of tianeptine after administration by the oral route. Biodegradable microparticles can also be used to formulate suitable controlled-release pharmaceutical compositions, for example as described in U.S. Pat. Nos. 5,354,566 and 5,733,566.

Generally, in humans oral or intravenous administration of the compounds of formula (I) in the form of a pharmaceutical formulation is the preferred route, especially oral administration.

Thus, the invention also provides a pharmaceutical composition for use in the treatment of respiratory depression in a human the composition comprising a compound of formula (I) as defined herein or a pharmaceutically acceptable salt thereof, or a pharmaceutically acceptable solvate of either entity, in admixture with a pharmaceutically acceptable adjuvant, diluent or carrier. Suitably, the invention also extends to a method of treating, such as inhibiting or reducing, respiratory depression in a human by administering such a pharmaceutical composition to a human. Suitably, the invention extends to the use of such a pharmaceutical composition for treating respiratory depression in a human.

Thus, in accordance with a further aspect the present invention provides the use of a compound of formula (I) as defined herein or a pharmaceutically acceptable salt thereof, or a pharmaceutically acceptable solvate of either entity, in the manufacture of a medicament for use in the treatment of respiratory depression in a human.

According to a further aspect of the invention there is provided a veterinary composition for use in the treatment of respiratory depression in an animal comprising a compound of formula (I) as defined herein, or a veterinarily acceptable salt thereof, or a veterinarily acceptable solvate of either entity, in admixture with a veterinarily acceptable adjuvant, diluent or carrier. Suitably, the invention also extends to a method of treating, such as inhibiting or reducing, respiratory depression in an animal by administering such a veterinary composition to an animal. Suitably, the invention extends to the use of such a veterinary composition for treating or preventing respiratory depression in an animal.

According to a further aspect, the present invention provides a method for reducing or inhibiting an undesired side effect of respiratory depression in a subject concomitant with the induction of the desired effect of analgesia, anaesthesia, or sedation, without affecting, in a clinically meaningful way, the desired effect of analgesia, anaesthesia, or sedation the method comprising the concomitant administration of a therapeutically effective amount of a central respiratory depressant sufficient to induce analgesia, anaesthesia, or sedation, and a therapeutically effective amount of a compound of formula (I), e.g. tianeptine, as defined herein or a pharmaceutically acceptable salt thereof, or a pharmaceutically acceptable solvate of either entity sufficient to reduce or inhibit respiratory depression.

Suitably, a therapeutically effect amount of a central respiratory depressant will depend on the identity of the central respiratory depressant and the mode of administration of the drug.

Typically, a therapeutically effective amount of such a drug may range from 50 µg/day (e.g. fentanyl) to 720 mg/day (e.g. morphine).

By the term "concomitant" or "concomitantly administered" as used herein means the administration of a first agent (e.g. a compound of formula (I) tianeptine) either before, during, or after the administration of a second agent (e.g. a central respiratory depressant). The order of administration of the agents is not critical, and the administration of the two agents may completely overlap, partially overlap, or not overlap. In embodiments where the administration periods of the two agents do not overlap, the administration is still concomitant if the second agent is administered during the bioactive period of the first agent.

The compounds of formula (I) may also be combined with other drugs, such as a central respiratory depressant as defined herein. Suitably, such compositions are useful for reducing or inhibiting an undesired side effect of respiratory depression associated with such drugs in a subject (i.e. animal) whilst simultaneously inducing the desired effect of analgesia, anaesthesia or sedation.

Thus according to a further aspect, the present invention provides a pharmaceutical composition for use in the treatment of respiratory depression and for the simultaneous production of analgesia, anesthesia or sedation in a human the pharmaceutical composition comprising the combination of (a) a therapeutically effect amount of a central respiratory depressant, preferably an opioid or opiate; and, (b) a therapeutically effective amount of a compound of formula (I) as defined herein or a pharmaceutically acceptable salt thereof, or a pharmaceutically acceptable solvate of either entity, in admixture with a pharmaceutically acceptable adjuvant, diluent or carrier. Suitably, when the central respiratory depressant is an opioid or opiate then the pharmaceutical composition may further include (c) a therapeutically effective amount of an opiate antagonist, such as naloxone or naltrexone, that is inactivated by first pass metabolism, such that the direct constipatory effect of the opiate or opioid on the gut muscle is inhibited. Typically, the ratio of the dosage of opiate antagonist to opiate agonist (i.e. when the central respiratory depressant is an opioid or opiate) is in the range of 0.02 to 3.00. Typically, the central respiratory depressant, preferably the opioid or opiate, is present in an amount of 0.1 to 30, preferably 1 to 20, more preferably 2 to 20, weight percent of the composition. Suitably, the pharmaceutical composition may comprise between from 50 µg to 720 mg, preferably 75 µg to 500 mg of the central respiratory depressant to be administered singly or two or more times a day. Typically, the compound of formula (I) is present in amount of the composition as defined herein. Preferably, such a pharmaceutical composition is for oral administration.

According to a preferred embodiment of the aforementioned pharmaceutical compositions, the central respiratory depressant (a), preferably an opioid or opiate, is present in an amount that if administered alone to the subject (i.e. human) would induce respiratory depression and the compound of formula (I) is present in amount such that the central respiratory depressant effect of the central respiratory depressant as a single agent is inhibited, preferably prevented, in the combination composition.

Thus according to a further aspect, the present invention provides a pharmaceutical composition for use in the treatment of respiratory depression and for the simultaneous production of analgesia, anesthesia or sedation in a human, the pharmaceutical composition comprising the combination of: (a) a therapeutically effect amount of a central respiratory depressant, preferably an opioid or opiate, that if administered alone to the subject (i.e. human) would induce respiratory depression; and, (b) a therapeutically effective amount of a compound of formula (I) as defined herein or a pharmaceutically acceptable salt thereof, or a pharmaceutically acceptable solvate of either entity, present in amount such that the central respiratory depressant effect of the central respiratory depressant as a single agent is inhibited, preferably prevented, in the combination composition, in admixture with a pharmaceutically acceptable adjuvant, diluent or carrier. Suitably, when the central respiratory depressant is an opioid or opiate then the pharmaceutical composition may further include (c) a therapeutically effective amount of an opiate antagonist, such as naloxone or naltrexone, that is inactivated by first pass metabolism, such that the direct constipatory effect of the opiate or opioid on the gut muscle is inhibited. Typically, the ratio of the dosage of opiate antagonist to opiate agonist (i.e. when the central respiratory depressant is an opioid or opiate) is in the range of 0.02 to 3.00. Preferably, such a pharmaceutical composition is for oral administration.

Suitably, the invention also extends to a method of producing analgesia, anesthesia or sedation in a human and for simultaneously treating (e.g. reducing or inhibiting) respiratory depression the method comprising administering a pharmaceutical composition comprising the combination of: (a) a therapeutically effect amount of a central respiratory depressant, preferably an opioid or opiate, that if administered alone to the subject (i.e. human) would induce respiratory depression; and, (b) a therapeutically effective amount of a compound of formula (I) as defined herein or a pharmaceutically acceptable salt thereof, or a pharmaceutically acceptable solvate of either entity, in admixture with a pharmaceutically acceptable adjuvant, diluent or carrier to the human. Suitably, the invention extends to the use of such a pharmaceutical composition for the production of analgesia, anesthesia or sedation in a human whilst simultaneously reducing or inhibiting induction of respiratory depression. Preferably, such a pharmaceutical composition is for oral administration.

For oral and parenteral administration to human patients, the daily dosage level of the compounds of formula (I) or salts or solvates thereof will usually be from 2 to about 600 mg/day, preferably from about 5 to about 400 mg/day, and more preferably about 10 to 300 mg/day.

Thus, for example, tablets or capsules of the compounds of formula (I) or salts or solvates thereof may contain from 2.5 mg to 250 mg of active compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

The invention will now be exemplified by the following non-limiting examples.

EXAMPLE 1

Tablet Formulation

In general a tablet formulation could typically contain between about 2.5 mg and 250 mg of a compound of formula (I) (or a salt thereof) whilst tablet fill weights may range from 50 mg to 1000 mg. An example formulation for a 250 mg tablet is illustrated below:

| Ingredient | % w/w |
| --- | --- |
| Tianeptine Na salt | 10 |
| Lactose | 65 |
| Starch | 21 |
| Croscarmellose Sodium | 3 |
| Magnesium Stearate | 2 |

EXAMPLE 2

Opiate-Induced Respiratory Depression (a) Assessment of the Respiratory Activity Whole-body plethysmography is used to assess respiratory rate ($f_R$, in breaths per minute) and tidal volume (VT, in microliters per gram) in conscious rats. Animals are placed in a recording chamber (~700 ml) flushed continuously with a humidified mixture of 79% nitrogen and 21% oxygen (temperature 22-24° C.). Level of carbon dioxide ($CO_2$) in the chamber is monitored online using a fast-response $CO_2$ analyser. Animals are allowed ~40 min to acclimatize to the chamber environment at normoxia-normocapnia (21% oxygen, 79% nitrogen and <0.3% $CO_2$) before measurements of baseline ventilation are taken.

(b) Model of Opioid-Induced Respiratory Depression

Respiratory depression is induced in conscious rats by intramuscular (10 mg/kg) administration of morphine.

(c) Data Acquisition and Analysis

Data are acquired using Power1401 interface, saved and analyzed off-line using Spike2 software (CED Limited, Cambridge, UK).

Parameters measured included $f_R$—respiratory rate (in breaths per minute); VT—tidal volume (in microliters per gram of body weight); VE—minute ventilation $f_R \times VT$ (in microliters per gram of body weight per minute).

The data were analysed by ANOVA followed by the Tukey-Kramer's post hoc test, Student's t-test, or non-parametric Wilcoxon-Mann-Whitney U test, as appropriate. Data are presented as means±SEM. Differences between the experimental groups with p<0.05 (i.e. the probability that this result arose by chance) were considered significant.

(d) Results

Figure 2:
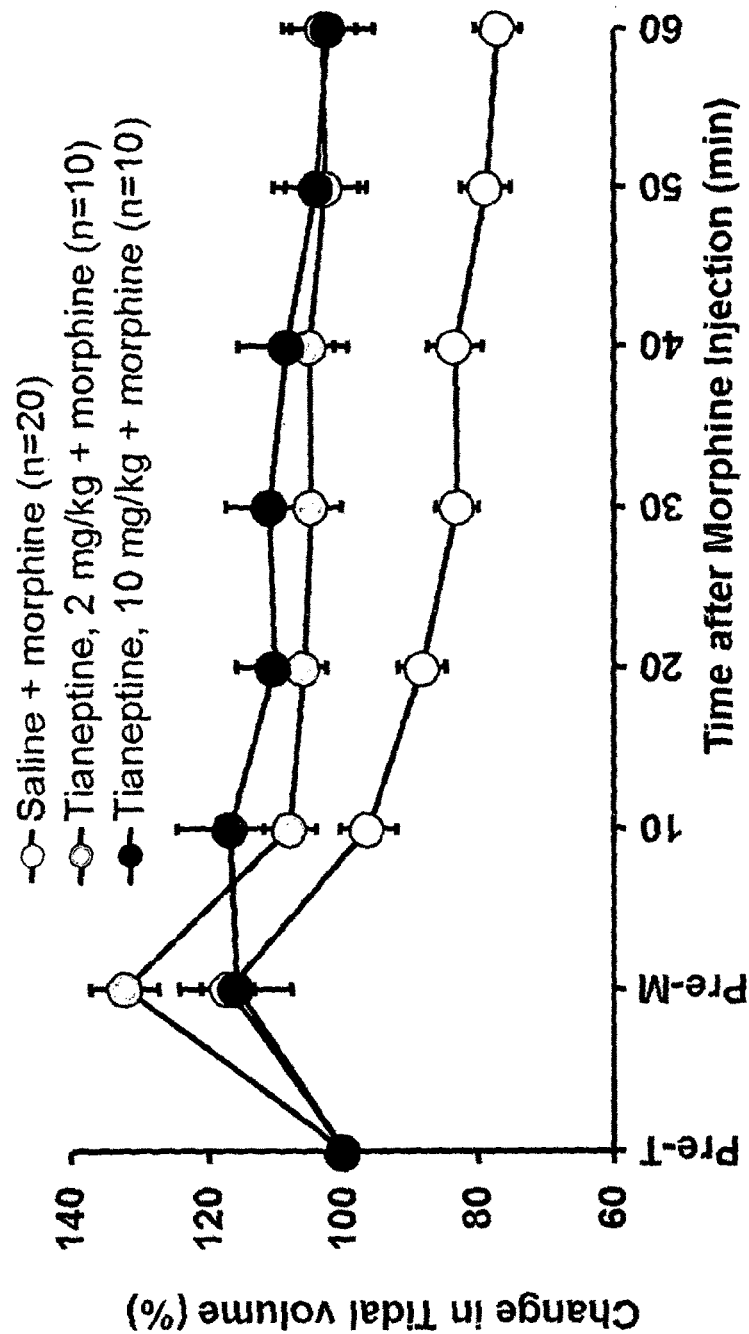
FIG. 2 depicts the change in tidal volume for (a) animals injected with morphine (10 mg/kg intramuscular) and saline only; (b) animals injected with tianeptine (2 mg/kg ip) and followed by morphine (10 mg/kg intramuscular); and (c) animals injected with tianeptine (2 mg/kg ip) and followed by morphine (10 mg/kg intramuscular).
Figure 3:
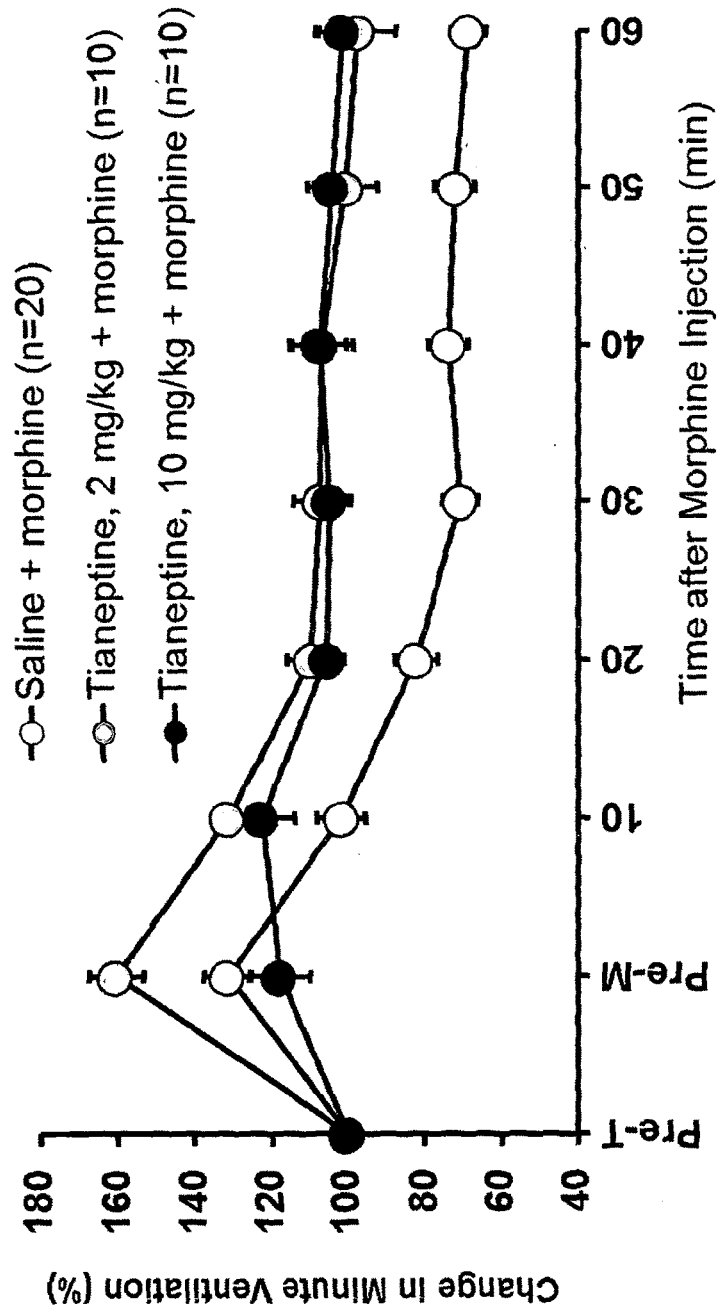
FIG. 3 depicts the change in minute ventilation for (a) animals injected with morphine (10 mg/kg intramuscular) and saline only; (b) animals injected with tianeptine (2 mg/kg ip) and followed by morphine (10 mg/kg intramuscular); and (c) animals injected with tianeptine (2 mg/kg ip) and followed by morphine (10 mg/kg intramuscular).

The summary of results are displayed in FIGS. 1 to 3 wherein:

FIG. 1 depicts the change in respiratory rate for (a) animals injected with morphine (10 mg/kg intramuscular) and saline only; (b) animals injected with tianeptine (2 mg/kg ip) and followed by morphine (10 mg/kg intramuscular); and (c) animals injected with tianeptine (2 mg/kg ip) and followed by morphine (10 mg/kg intramuscular);

FIG. 2 depicts the change in tidal volume for (a) animals injected with morphine (10 mg/kg intramuscular) and saline only; (b) animals injected with tianeptine (2 mg/kg ip) and followed by morphine (10 mg/kg intramuscular); and (c) animals injected with tianeptine (2 mg/kg ip) and followed by morphine (10 mg/kg intramuscular); and, FIG. 3 depicts the change in minute ventilation for (a) animals injected with morphine (10 mg/kg intramuscular) and saline only; (b) animals injected with tianeptine (2 mg/kg ip) and followed by morphine (10 mg/kg intramuscular); and (c) animals injected with tianeptine (2 mg/kg ip) and followed by morphine (10 mg/kg intramuscular).

The results demonstrate that in conscious animals, tianeptine (2 mg/kg, ip) induced a significant (p<0.05) increase (by ~30%) in the respiratory activity 5 min after administration (FIGS. 1 to 3). Subsequent injection of morphine (10 mg/kg) 5 minutes after tianeptine markedly reduced the respiratory activity in tianeptine-treated animals, however, ventilation did not decrease below the baseline. Thus, tianeptine appears to prevent morphine-induced respiratory depression. An increase in the respiratory activity was not observed in rats injected with tianeptine at 10 mg/kg, however morphine-induced respiratory depression was prevented (FIGS. 1 to 3).

The elevation of respiratory activity due to tianeptine at 2 mg/kg ip prior to administration of morphine is taken to be indicative of potential utility in respiratory depression due to a disease rather than due to a drug.

EXAMPLE 3

Rett's Syndrome (a) Animals

Methyl-CpG-binding protein 2 (Mecp) null mice were of the B6.129P2(C)-Mecp2$^{tm1.1Bird}$ strain. Mice were produced and genotyped using published methods (Miralvès J, Magdeleine E, Joly E. Design of an improved set of oligonucleotide primers for genotyping MeCP2$^{tm1.1Bird}$ KO mice by PCR. Mol Neurodegener. 2007; 2:16; Bissonnette J M, Knopp S J. Separate respiratory phenotypes in methyl-CpG-binding protein 2 (Mecp2) deficient mice. Pediatr Res. 2006; 59:513-518).

(b) Drug Treatment

Drug treated animals were administered tianeptine (10 mg/kg) in saline by i.p injection; control measurements were based on the breathing pattern of animals pre-treatment.

(c) Plethysmography

Breathing was recorded over a 60 min control period following drug treatment in the same way as for the respiratory depression experiments, with the same equipment and software. After the recording sessions, mice were euthanized with $CO_2$.

(d) Results

The respiratory frequency patterns of drug treated mice were analysed before and after drug treatment. There was an overall reduction of the peak dominant frequency from 5.6 to 4.8 Hz (p=0.037, Student's paired t test) which indicates, in line with previous work (Ogier, M. et al. Brain-Derived Neurotrophic Factor Expression and Respiratory Function Improve after Ampakine Treatment in a Mouse Model of Rett Syndrome. J. Neurosci. 27, 10912-10917 (2007)), a benefit in Rett's syndrome.

The invention claimed is:

1. A method of treating respiratory depression in a mammal comprising administration of a compound of formula (I), or a pharmaceutically or veterinarily acceptable salt thereof, said compound of formula (I):

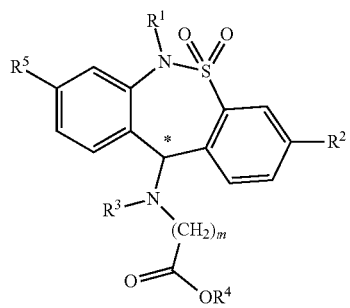

wherein:
$R^1$ and $R^3$ each independently represent, at each occurrence when used herein, H or $C_1$ to $C_6$ alkyl;
$R^2$ and $R^5$ each independently represent, at each occurrence when used herein, H or halo;
$R^4$ represents H or $C_1$ to $C_6$ alkyl; and,
m is an integer of 2 to 12 inclusive.

2. The method of claim 1, wherein $R^1$ in the compound of formula (I) represents a $C_1$ to $C_4$ alkyl group.

3. The method of claim 1, wherein $R^2$ in the compound of formula (I) represents halo.

4. The method of claim 1, wherein $R^3$ in the compound of formula (I) represents H.

5. The method of claim 1, wherein $R^4$ in the compound of formula (I) represents H.

6. The method of claim 1, wherein $R^5$ in the compound of formula (I) represents H.

7. The method of claim 1, wherein m in the compound of formula (I) is an integer from 2 to 6 inclusive.

8. The method of claim 1, wherein the compound of formula (I) is tianeptine, wherein in a compound of formula (I), $R^1$ is methyl, $R^2$ is chloro, $R^3$ is hydrogen, $R^4$ is hydrogen, $R^5$ is hydrogen, and m is 6.

9. The method of claim 1, wherein the compound of formula (I) is the MC5 metabolite of tianeptine, wherein in a compound of formula (I), $R^1$ is methyl, $R^2$ is chloro, $R^3$ is hydrogen, $R^4$ is hydrogen, $R^5$ is hydrogen, and m is 4.

10. The method of claim 1, wherein the compound of formula (I) is in the (R)-enantiomeric form in respect of the aliphatic carbon marked with an asterisk (*) and substantially free of the (S)-enantiomeric form in respect of the aliphatic carbon marked with an asterisk (*).

11. The method of claim 1, wherein the compound of formula (I) is in the (S)-enantiomeric form in respect of the aliphatic carbon marked with an asterisk (*) and substantially free of the (R)-enantiomeric form in respect of the aliphatic carbon marked with an asterisk (*).

12. The method of claim 1, further comprising administering a therapeutically effective amount of a central respiratory depressant so as to produce simultaneous analgesia, anesthesia or sedation, wherein the central respiratory depressant is an opioid or opiate selected from the group consisting of alfentanil, buprenorphine, carfentanil, codeine, dihydrocodeine, diprenorphine, ecgonine, etorphine, fentanyl, heroin, hydrocodone, hydromorphone, laevo-alpha-acetylmethadol (LAAM), levorphanol, meperidine, methadone, morphine, nalbuphine, beta-hydroxy-3-methylfentanyl, oxycodone, oxymorphone, pentazocine, propoxyphene, remifentanil, sufentanil, thebaine, tilidine, and tramadol.

13. The method as claimed in claim 12 further including a therapeutically effective amount of an opiate antagonist that is inactivated by first pass metabolism, such that the direct constipatory effect of the opiate or opioid on the gut muscle is inhibited, wherein the opiate antagonist is selected from the group consisting of naloxone and naltrexone.

14. The method of claim 1, wherein the respiratory depression results from the administration of a central respiratory depressant to the mammal and the central respiratory depressant is an opioid or opiate selected from the group consisting of alfentanil, buprenorphine, carfentanil, codeine, dihydrocodeine, diprenorphine, ecgonine, etorphine, fentanyl, heroin, hydrocodone, hydromorphone, laevo-alpha-acetylmethadol (LAAM), levorphanol, meperidine, methadone, morphine, nalbuphine, beta-hydroxy-3-methylfentanyl, oxycodone, oxymorphone, pentazocine, propoxyphene, remifentanil, sufentanil, thebaine, tilidine, and tramadol.

15. The method of claim 1, wherein the treatment of respiratory depression results from a medical condition selected from the group consisting of: central sleep apnea, stroke-induced central sleep apnea, obstructive sleep apnea, sleep apnea resulting from Parkinson's disease, congenital hypoventilation syndrome, obesity hyperventilation syndrome, sudden infant death syndrome, Rett's syndrome, Cheyne-Stokes respiration, Biot's breathing, Ondines Curse, spinal muscular atrophy, amyotrophic lateral sclerosis, Prader-Willi's syndrome, spinal cord injury and traumatic brain injury.

16. The method of claim 1, wherein the mammal is a human.

17. The method of claim 1, further comprising administering an acceptable adjuvant, diluent or carrier with the compound of formula (I).

18. The method of claim 1, wherein the treatment of respiratory depression in the mammal is achieved by oral or intravenous administration of the compound of formula (I).

* * * * *